United States Patent
Ganguli et al.

(10) Patent No.: US 9,572,893 B2
(45) Date of Patent: Feb. 21, 2017

(54) NANOCOMPLEX CONTAINING CATIONIC PEPTIDE FOR BIOMOLECULE DELIVERY

(71) Applicant: Council of Scientific and Industrial Research, New Delhi (IN)

(72) Inventors: Munia Ganguli, Delhi (IN); Anita Mann, Delhi (IN); Vasundhara Shukla, Delhi (IN); Manika Vij, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 8 days.

(21) Appl. No.: 14/441,360

(22) PCT Filed: Nov. 6, 2013

(86) PCT No.: PCT/IN2013/000683
§ 371 (c)(1),
(2) Date: May 7, 2015

(87) PCT Pub. No.: WO2014/072999
PCT Pub. Date: May 15, 2014

(65) Prior Publication Data
US 2015/0343086 A1    Dec. 3, 2015

(30) Foreign Application Priority Data
Nov. 7, 2012  (IN) .............. 3435/DEL/2012

(51) Int. Cl.
*A61K 47/48*   (2006.01)
*C12N 15/87*   (2006.01)
*A61K 48/00*   (2006.01)

(52) U.S. Cl.
CPC ... *A61K 47/48315* (2013.01); *A61K 47/48323* (2013.01); *C12N 15/87* (2013.01); *A61K 48/00* (2013.01); *C07K 2319/10* (2013.01); *Y10T 428/2982* (2015.01)

(58) Field of Classification Search
CPC ............... A61K 47/48315; A61K 47/48323; A61K 48/00; C07K 2319/10; C12N 15/87; Y10T 428/2982
USPC ............... 428/402; 435/455; 530/322, 326
See application file for complete search history.

(56) References Cited

U.S. PATENT DOCUMENTS
2011/0053829 A1    3/2011   Baumhof et al.

FOREIGN PATENT DOCUMENTS

| WO | WO-02/053759 | 7/2002 |
| WO | WO-2012/113513 | 8/2012 |
| WO | WO-2014/072999 | 5/2014 |

OTHER PUBLICATIONS

"International Application No. PCT/IN2013/000683, International Preliminary Report on Patentability dated Jan. 5, 2015", 20 pgs.
"International Application No. PCT/IN2013/000683, Written Opinion mailed Apr. 17, 2014", 8 pgs.

(Continued)

*Primary Examiner* — Janet Epps-Smith
(74) *Attorney, Agent, or Firm* — Schwegman Lundberg & Woessner, P.A.

(57) ABSTRACT

The present invention relates to developing an optimally efficient arginine-histidine-cysteine based peptide comprising nanocomplex that can deliver biomolecules across varied cell lines without any oxidative procedure through formation of monodisperse nanoparticles with sizes ranging between 50 and 110 nm.

13 Claims, 9 Drawing Sheets

(56) References Cited

OTHER PUBLICATIONS

El-Sayed, Ayman, et al., "Delivery of Macromolecules Using Arginine-Rich Cell-Penetrating Peptides: Ways to Overcome Endosomal Entrapment", *The AAPS Journal*, 11(1), (2008), 13-22.
Hart, Stephen L., "Multifunctional nanocomplexes for gene transfer and gene therapy", *Cell Biology and Toxicology*, 26(1), (2010), 69-81.
Howard, Kenneth A., "Delivery of RNA interference therapeutics using polycation-based nanoparticles", *Advanced Drug Delivery Reviews*, 61, (2009), 710-730.
Lo, Seong L., et al., "An endosomolytic Tat peptide produced by incorporation of histidine and cysteine residues as a nonviral vector for DNA transfection", *Biomaterials*, 29(15), (2008), 2408-2414.
Mann, Anita, et al., "Peptides in DNA delivery: current insights and future directions", *Drug Discovery Today*, (Dec. 2007), 152-160.
Midoux, Patrick, et al., "Chemical vectors for gene delivery: a current review on polymers, peptides and lipids containing histidine or imidazole as nucleic acids carriers", *British Journal of Pharmacology*, 157(2), (2009), 166-178.
Mintzer, Meredith A., et al., "Nonviral Vectors for Gene Delivery", *Chem. Rev.*, 109(2), (2009), 259-302.
Morris, May C., et al., "Translocating peptides and proteins and their use for gene delivery", *Current Opinion in Biotechnology*, 11, (2000), 461-466.
Petros, Robby A., et al., "Strategies in the design of nanoparticles for therapeutic applications", *Nature Reviews Drug Discovery*, 9, (Aug. 2010), 615-627.
Remaut, Katrien, et al., "Nucleic acid delivery: Where material sciences and bio-sciences meet", *Materials Science and Engineering*, R 58, (2007), 117-161.
Rubanyi, Gabor M., "The Future of Human Gene Therapy", *Molecular Aspects of Medicine*, 22, (2001), 113-142.
Saccardo, Paolo, et al., "Peptide-mediated DNA condensation for non-viral gene therapy", *Biotechnology Advances*, 27, (2009), 432-438.

Vázquez, Esther, et al., "Peptide-assisted traffic engineering for nonviral gene therapy", *Drug Discovery Today*, 13(23/24), (Dec. 2008), 1067-1074.
Won, Young-Wook, et al., "Poly(oligo-D-arginine) With Internal Dissulfide Linkages as a Cytoplasm-sensitive Carrier for siRNA Delivery", *Molecular Therapy*, 19(2), (Feb. 2011), 372-380.
Won, Young-Wook, et al., "Reducible Poyl(oligo-D-argnine) for Enhanced Gene Expression in Mouse Lung by Intratracheal Injection", *Molecular Therapy*, 18(4), (Apr. 2010), 734-742.
"International Application No. PCT/IN2013/000683, International Search Report mailed Apr. 17, 2014", (Apr. 17, 2014), 5 pgs.
"International Application No. PCT/IN2013/000683, Request for Demand and Article 34 Amendments filed Sep. 4, 2014", (Sep. 4, 2014), 12 pgs.
Kim, Hyun Hee, et al., "Basic peptide system for efficient delivery of foreign genes", Biochimica et Biophysica Acta 1640 (2003) 129-136, (Mar. 11, 2003), 129-136.
Liu, Betty R., et al., "Intracellular delivery of quantum dots mediated by a histidine- and arginine-rich HR9 cell-penetrating peptide through the direct membrane translocation mechanism", Biomaterials, vol. 32, Issue 13, May 2011, pp. 3520-3537, (May 2011), 3520-3537.
Mann, Anita, "Differences in DNA condensation and release by lysine and arginine homopeptides govern their DNA delivery efficiencies", Mol Pharm. 2011; 8(5):1729-41, (Oct. 3, 2011), 1729-1741.
Mann, Anita, et al., "Linear Short Histidine and Cysteine Modified Arginine Peptides Constitute a Potential Class of DNA Delivery Agents", Molecular Pharmaceutics (Impact Factor: 4.79). Jan. 2014; 11(3), 683-696, (Mar. 3, 2014), 683-696.
Martin, Molly E., et al., "Peptide-guided Gene Delivery", The AAPS Journal 2007; 9 (1) Article 3 (http://www.aapsj.org), (Feb. 9, 2007), 12 pgs.
Sharma, Rajpal, "Insight into the Role of Physicochemical Parameters in a Novel Series of Amphipathic Peptides for Efficient DNA Delivery", Molecular Pharmaceutics (Impact Factor: 4.79). Jun. 2013; 10(7), 2588-2600, (Jul. 1, 2013), 2588-2600.
Sharma, Rajpal, "Structural rearrangements and chemical modifications in known cell penetrating peptide strongly enhance DNA delivery efficiency", Journal of Controlled Release, vol. 157, Issue 2, Jan. 30, 2012, pp. 260-271, (Jan. 30, 2012), 260-271.

| Parameters | C-R₅H₄R₄H₃-C | C-R(RH)₇R-C |
|---|---|---|
| Z-Avg (nm) | 68.34 | 77.75 |
| Pd Index | 0.233 | 0.221 |
| Zeta Potential (mV) | 42.8 | 24.6 |

NANOCOMPLEX CONTAINING CATIONIC PEPTIDE FOR BIOMOLECULE DELIVERY

PRIORITY CLAIM TO RELATED APPLICATIONS

This application is a U.S. national stage application filed under 35 U.S.C. §371 from International Application Serial No. PCT/IN2013/000683, which was filed 6 Nov. 2013, and published as WO 2014/072999 on 15 May 2014, and which claims priority to India Application No. 3435/DEL/2012, filed 7 Nov. 2012, which applications and publication are incorporated by reference as if reproduced herein and made a part hereof in their entirety, and the benefit of priority of each of which is claimed herein.

FIELD OF THE INVENTION

The present invention relates to a nanocomplex containing cationic peptide for delivery of biomolecules into a eukaryotic cell. The present invention specifically relates to a nanocomplex containing arginine-histidine-cysteine based peptide sequences (SEQ ID NO.: 1 and SEQ ID NO.: 2) that can deliver nucleic acid to a eukaryotic cell.

BACKGROUND OF THE INVENTION

The knowledge about the human genome in the last decade has helped in our understanding of the causes and molecular mechanisms for manifestation of various diseases. It is a well-accepted fact that the treatment for several monogenic and acquired genetic disorders as well as complex diseases like cancer can be fully or partially achieved by different types of gene therapy approaches [Rubanyi G M, 2001; Howard K A, 2009; Petros R A et. al., 2010]. Adopting such approaches is limited by the availability of safe and efficient vectors which can deliver the desired nucleic acid for gene expression/suppression to affected cells/tissues in the body. Viral gene delivery systems have been largely explored and account for more than 70% of clinical trials but their practical applicability to the clinics is still questionable due the associated risks like insertional mutagenesis and immune activation [Mark A K et. al., 2003]. Lipid and polymer based non-viral vectors provide a safer alternative and can also carry large cargo molecules unlike viral vectors but are of limited use because of their inability to overcome all the barriers encountered during in vivo delivery of nucleic acids and long term toxicity and biocompatibility issues. Additionally their synthesis demands specialized expertise and can often result in limited product yield posing economic constraints [Mintzer M A et. al., 2009; Remaut K et. al., 2007].

A more recent rational approach is the integration of different non-viral vectors such that they can complement each other's functions and systematically cross the hurdles encountered during in vivo gene delivery. Peptides are the best choice in this regard since different peptides possess the inherent ability to cross various cellular barriers like plasma, endosomal and nuclear membranes [Remaut K et. al., 2007; Mintzer M A et. al., 2009]. Peptides can also package different forms and sizes of nucleic acids to form nanocomplexes, and serve as cellular targeting ligands. Other advantages such as ease of synthesis and chemical modifications, relatively low toxicity and immunogenicity make peptides an attractive class of non-viral nucleic acid delivery agents [Vazquez E et. al., 2008; Martin M E et. al., 2007; Morris M C et. al., 2000; Hart S L et. al., 2010; Mann A et. al., 2008].

Peptides have been described in the literature for delivery of biomolecules like DNA and siRNA. Of these, lysine and arginine-rich peptides are the most promising vectors for plasmid DNA delivery since they can efficiently condense DNA and form nanocomplexes to prevent enzymatic degradation inside the cell [Mann A et. al., 2007]. In addition, arginine peptide show strong cellular uptake [Biessen E A L et. al., 2004; Wang S et. al., 2008; Harashima H et. al., 2009; Kim Y H et. al., 2009]. Arginine homopeptides possess better DNA condensation and release balance than their cognate lysine variants and thus are more efficient. However, the efficiency of delivery of a large cargo like plasmid DNA in the form of a nanocomplex by lysine and arginine homopeptides is rather low because of their inability to overcome the endosomal barrier effectively. Modification of lysine peptides in these nanocomplexes with histidines in linear as well as branched form have been shown to add endosomal escape property to the DNA condensing system [Kichler et. al., 2007]. However, such systems involve complicated design and synthesis steps and are not very efficient.

There is a need to design nanocomplexes containing cationic peptide which are able to overcome all the barriers for intracellular entry by showing high cellular uptake, efficient endosomal escape and high transfection efficiency with low toxicity.

In the present work we have explored various arginine-histidine-cysteine combinations and have developed nanocomplexes containing two novel cationic peptides with combinations of 9 arginine residues, 7 histidine residues and 2 cysteine residues at both ends that can efficiently overcome endosomal barrier but retain their DNA-condensation and release balance. Arginines have been used as condensing moieties, histidines are involved in efficient endosomal escape and the addition of cysteines further enhances the DNA condensation and release balance possibly through formation of reducible cross-linkages. These nanocomplexes show remarkable efficiency of plasmid DNA delivery comparable to commercially available transfection reagents in various cell lines including the ones which are tough to transfect. These particular nanocomplexes comprising linear arginine-histidine-cysteine sequences of short length (as described in the sequence listings) with high DNA delivery efficiency and low toxicity are completely unique.

Lysine/Arginine-histidine-cysteine nanocomplex systems listed in the literature are either (a) in the form of reducible polycations (RPCs) where the peptide has been polymerized before making a nanocomplex with the DNA or (b) the peptide-DNA nanocomplex is oxidized [Wang S et. al., 2008; Kim Y H et. al., 2009; Kim Y H et. al., 2010]. Such oxidation steps are not required in our nanocomplex system. This is an obvious advantage of our system over existing ones.

OBJECTS OF INVENTION

The main object of the present invention is to provide a nanocomplex using cationic peptides comprising arginine, histidine and cysteine residues useful for efficient transfection of biomolecules.

Another object of the present invention is to develop cationic peptide to non-covalently interact with large DNA and make nanocomplexes.

Another objective of this invention is to develop a nanocomplex in which oxidation is not required for achieving increased transfection efficiency i.e. 1-2 orders higher with respect to known commercial agents.

Further objective is to provide a nanocomplex containing cationic peptides which can transfect a variety of cell lines with efficiency comparable or better than commercial agents.

Another objective of the present invention is to integrate the endosomal escape property to the nanocomplex resulting in endosome buffering at low pH and better biomolecule delivery efficiency.

Another objective is to develop a nanocomplex containing simple and linear and efficient cationic peptide which has negligible cellular toxicity.

SUMMARY OF INVENTION

Accordingly, the present invention relates to a nanocomplex containing cationic peptide which efficiently transfects biomolecules into a eukaryotic cell.

The present invention provides a unique combination of arginine, histidine and cysteine based nanocomplex system with unique arrangement of residues that gives high transfection activity.

In an embodiment of the invention a nanocomplex containing cationic peptide for biomolecule delivery characterised in containing peptide sequences comprising 9-arginines, 7-histidines, and 2-cysteines.

In an embodiment of the invention a nanocomplex wherein the peptide has sequence in the arrangement of $CR_5H_4R_4H_3C$ (SEQ ID NO.:1) and $CR(RH)_7RC$ (SEQ ID NO.: 2).

In an embodiment of the invention a nanocomplex wherein the biomolecule is selected from the group comprising of a DNA, RNA, an antisense nucleotide, an aptamer, a protein, a glycoprotein, a polypeptide, a carbohydrate or a mixture or adduct of any two or more of these.

In an embodiment of the invention wherein the size of the biomolecule is in the range of 3 kbp to 7 kbp.

In an embodiment of the invention a nanocomplex has a size in the range of 50-110 nm.

In an embodiment of the invention a nanocomplex gives maximal transfection efficiency of 7-9 orders in RLU/mg protein with minimal cytotoxicity.

In yet another embodiment of the invention a method for transfection of cell using the nanocomplex characterized in having no prior oxidation step.

In yet another embodiment of the invention a method of preparing the nanocomplex comprising steps:
a. providing SEQ ID NO.: 1 and SEQ ID NO.: 2;
b. providing a biomolecules to be transfected;
c. diluting the peptide 10-100 µl obtained in step (a) and DNA 20-50 ng/µl obtained in step (b) in water such that peptide-DNA charge ratio is 0.25-20;
d. adding DNA solution obtained in step (b) drop-wise to an equal volume of the peptide dilution while vortexing;
e. incubating solution obtained in step (d) for 30 min to 1 h at room temperature.

The present invention relates to the nanocomplex which has DNA condensation (at charge ratio=1.5-2.0) and release (at wt. of anionic agent/wt. of peptide ratio=0.5-1.0) balance (by using arginines and cysteine amino acids) along with endosomal escape property (by using histidines which has the unique ability of endosome buffering at low pH).

In a further embodiment use of nanocomplex for efficient delivery of nucleic acids into eukaryotic cells with minimal toxicity.

In a further embodiment use of nanocomplex as a peptide based carrier system.

In a further embodiment a kit useful for delivering biomolecules into a cell, said kit comprising of peptides and an instruction manual.

In a further embodiment use of nanocomplex for protection of biomolecules in presence of serum and efficient transfection in eukaryotic cells in serum containing medium.

In a further embodiments use of the nanocomplex for efficient transfection of biomolecules into multiple cell lines.

In yet another embodiment to the present invention, the nanocomplex can efficiently deliver biomolecules into multiple cell lines; comparable to commercially available transfection agents while showing less cytotoxicity implying the prospect of in vivo applicability.

In an embodiment to the present invention, the nanocomplex system comprising of 9-arginines, 7-histidines, 2-cysteines in the arrangement of $CR(RH)_7RC$ gives maximal transfection efficiency [7-9 orders in RLU/mg protein] with minimal cytotoxicity.

In an embodiment to the present invention, the nanocomplex system comprising of 9-arginines, 7-histidines, 2-cysteines in the arrangement of $CR_5H_4R_4H_3C$ gives maximal transfection efficiency [7-9 orders in RLU/mg protein] with minimal cytotoxicity.

In still another embodiment to the present invention, wherein the transfection efficiency of nanocomplex containing $(CR(RH)_7RC)$ at charge ratio 10.0 is five folds higher with respect to $R_9$ homopeptide comprising nanocomplex and three folds higher with respect to $R(RH)_7R$ peptide comprising nanocomplex in case of CHO-K1 cells and four folds higher with respect to $R_9$ homopeptide comprising nanocomplex and three folds higher with respect to $R(RH)_7R$ peptide comprising nanocomplex in case of MCF-7 cells.

In an embodiment to the present invention, wherein the transfection efficiency of peptide comprising nanocomplex transfection agent $(CR_5H_4R_4H_3C)$ at charge ratio 10.0 is four folds higher with respect to $R_9$ homopeptide comprising nanocomplex and two folds higher with respect to $R_5H_4R_4H_3$ peptide comprising nanocomplex in case of CHO-K1 cells and three folds higher with respect to $R_9$ homopeptide comprising nanocomplex and two folds higher with respect to $R_5H_4R_4H_3$ peptide comprising nanocomplex in case of MCF-7 cells.

In an embodiment to the present invention, the transfection efficiency of peptide comprising nanocomplex transfection agent is higher or similar as compared to commercially available transfection agents depending upon the system/cell line as well as charge ratio. Though both the peptide comprising nanocomplex systems show efficient transfection efficiency at charge ratio 5.0 but they give slightly increased transfection efficiency at charge ratio 10.0 without compromising the cellular morphology.

In still another embodiment to the present invention, the transfection efficiency of $(CR(RH)_7RC)$ nanocomplex is comparable to Lipofectamine 2000™ as seen in both HACAT and CHO-K1 cells whereas it is higher as compared to Cellfectin in both the cell lines. With respect to Superfect™ increase is evident only in CHO-K1 cells while it is comparable in case of Hacat cells at charge ratio 10.0.

In still another embodiment to the present invention, the transfection efficiency of $(CR_5H_4R_4H_3C)$ nanocomplex is comparable to Lipofectamine 2000™ as seen in both HACAT and CHO-K1 cells whereas it is higher as compared to Cellfectin™ in both the cell lines. With respect to Superfect™ increase is evident only in CHO-K1 cells while it is comparable in case of Hacat cells at charge ratio 10.0.

In an embodiment to the present invention wherein the peptide comprising nanocomplex transfection agent (CR (RH)₇RC) shows 80-90% cell viability as compared to commercial agents Lipofectamine 2000™ and Superfect™ which shows 70-80% cell viability and is comparable to Cellfectin™ in Hacat cells. In case of CHO-K1 cells, the peptide comprising nanocomplex transfection agent (CR (RH)₇RC) shows 70-80% cell viability as compared to commercial agent Lipofectamine 2000™ which shows 40-50% cell viability and is comparable to Cellfectin™ and Superfect™ transfection agents.

In an embodiment to the present invention wherein the peptide comprising nanocomplex transfection agent (CR$_5$H$_4$R$_4$H$_3$C) shows 80-90% cell viability as compared to commercial agents Lipofectamine 2000™ and Superfect™ which shows 70-80% cell viability and is comparable to Cellfectin™ in Hacat cells. In case of CHO-K1 cells, the peptide comprising nanocomplex transfection agent (CR$_5$H$_4$R$_4$H$_3$C) shows 80-90% cell viability as compared to commercial agent Lipofectamine 2000™ which shows 40-50% cell viability and is comparable to Cellfectin™ and Superfect™ transfection agents.

In an embodiment to the present invention the peptide comprising nanocomplex transfection agents (CR(RH)₇RC) and (CR$_5$H$_4$R$_4$H$_3$C) exhibit serum stability and give consistently high transfection efficiency [5-7 orders in RLU/mg protein] in the presence of 10% serum concentration.

Another aspect of invention is use of peptide comprising nanocomplex transfection agent for efficient delivery of nucleic acids such as plasmid DNA which can be extended to other oligonucleotides and similar into the cells.

The invention also provides a process of non oxidative preparation of peptide comprising nanocomplex transfection agent giving high transfection activity with minimal or no cytotoxicity.

BRIEF DESCRIPTION OF FIGURES

[Left Panel] Lane 1 (ctrl) represents the native uncomplexed plasmid DNA. The other lanes show DNA complexed with increasing amount of peptide to form a nanocomplex expressed as increasing charge ratio. [Right Panel] Lane 1 is uncomplexed plasmid DNA, Lane 2 is only nanocomplex (charge ratio 10.0) and subsequent lanes are the nanocomplex with increasing amount of heparin (mentioned as anionic agent/peptide: wt/wt ratio).

FIG. 3: Cell viability measured via MTT assay and CellTitreGLO assay. CHO-K1 cells and HACAT cells were treated with arginines-histidine-cysteine based peptides comprising nanocomplexes (at charge ratio 10.0) and a Lipofectamine™/Cellfectin™/Superfect™-DNA complex for 4 hours and cell viability was assessed after 24 hours. Untreated cells are taken as control and their absorbance (in the presence of MTT reagent and cell titre GLO reagent) is set as 100% and relative decrease in absorbance is taken as measure of cell viability.

DETAILS OF THE INVENTION

Figure 1A:
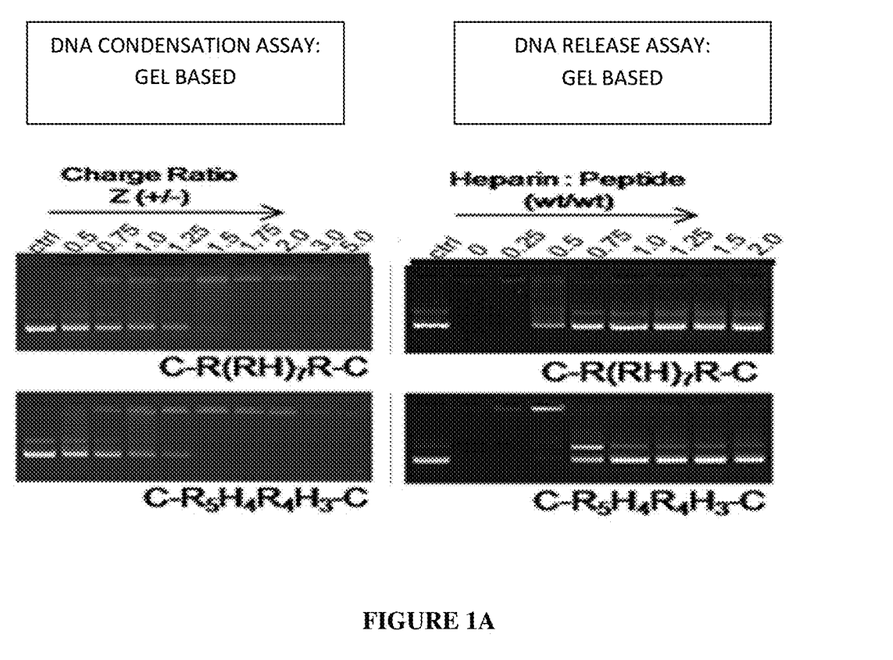
FIG. 1A: Relative DNA condensation ability of arginines-histidine-cysteine based peptides comprising nanocomplexes measured using gel retardation assay [Left Panel] and stability of arginines-histidine-cysteine based peptides comprising nanocomplexes against anionic challenge as measured by DNA release in the presence of increasing concentration of heparin [Right Panel].
Figure 1B:
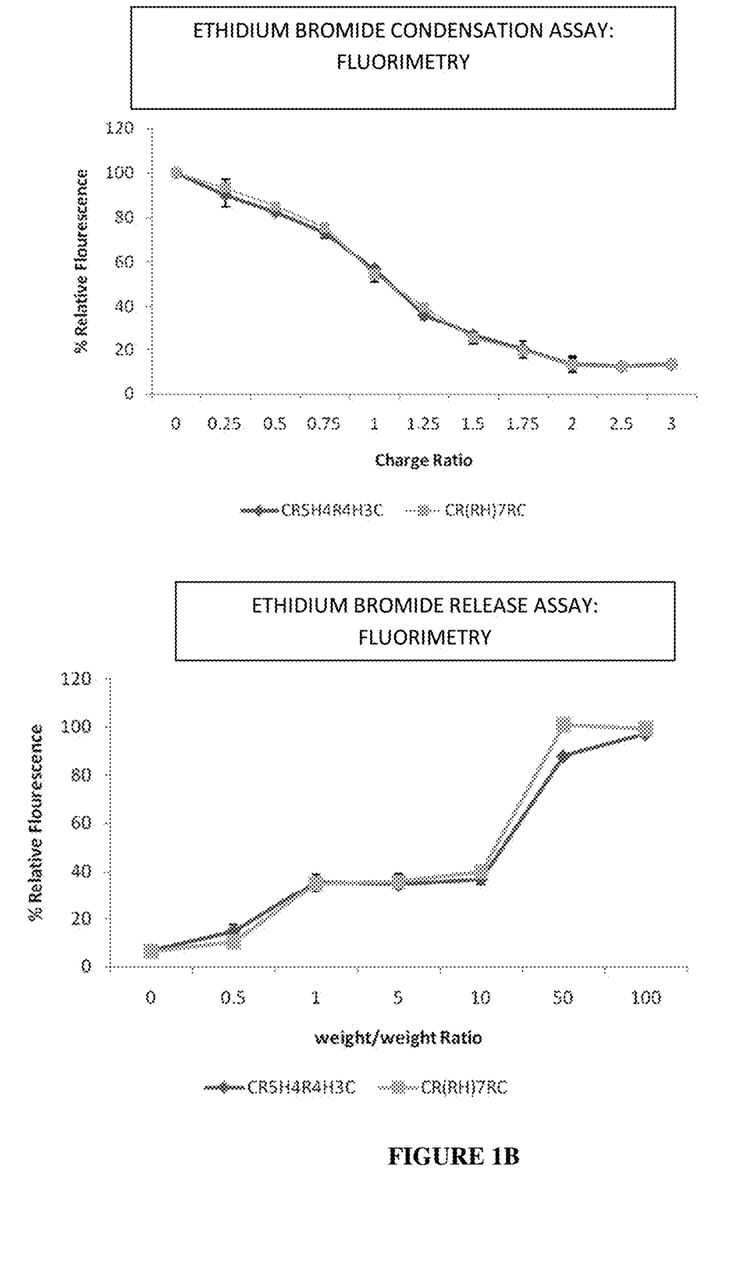
FIG. 1B: Relative DNA condensation ability [Left Panel] and stability against anionic challenge [Right Panel] of arginines-histidine-cysteine based peptides comprising nanocomplexes measured using fluorimetry based EtBr assay. The fluorescence of free uncomplexed DNA is set as maximum i.e 100% and relative decrease or increase in fluorescence is measured in DNA condensation and stability assays respectively.
Figure 1C:
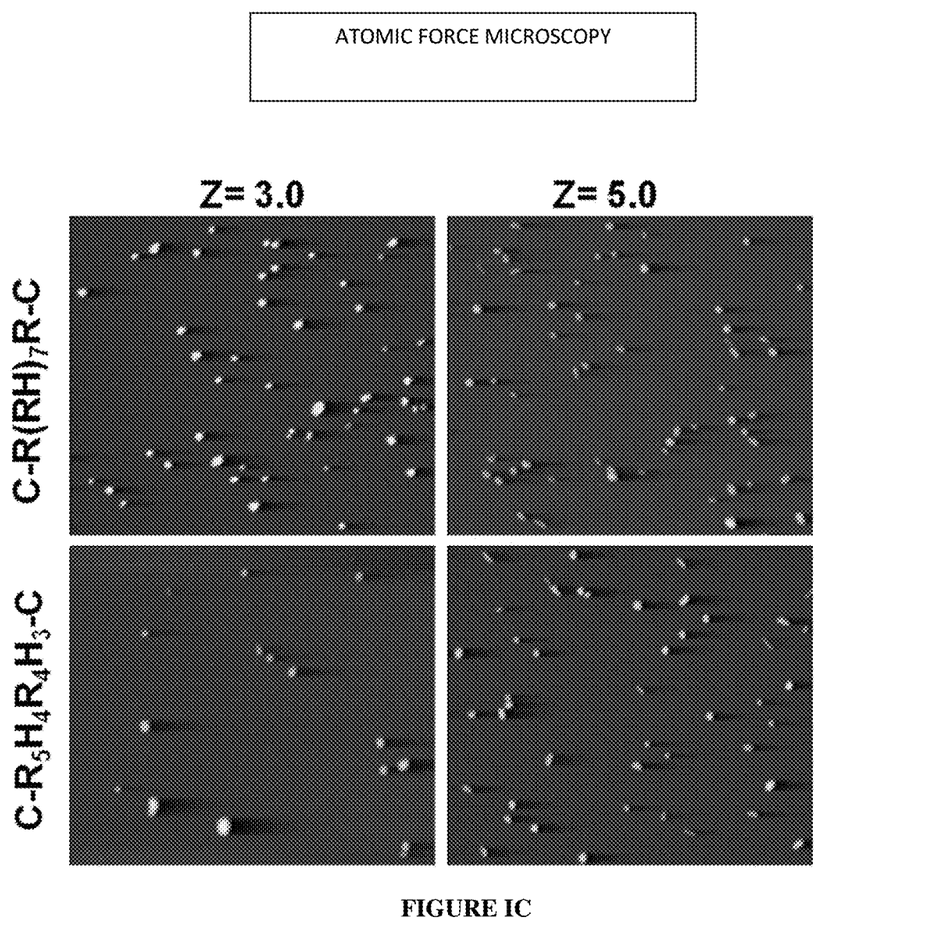
FIG. 1C: Representative Atomic force microscopy (AFM) images of arginines-histidine-cysteine nanocomplexes prepared at charge ratio 3.0 and 5.0 (image size is 4 µm×4 µm).
Figure 1D:
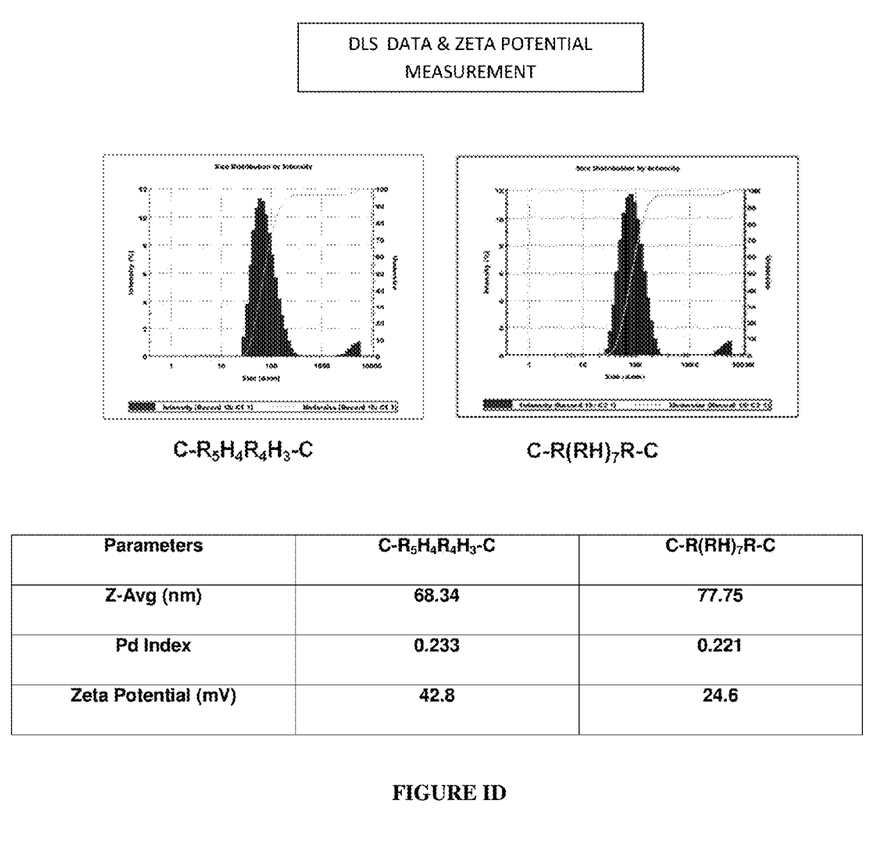
FIG. 1D: Representative Dynamic Light Scattering images and zeta potential data of arginines-histidine-cysteine nanocomplexes at charge ratio 10.0.
Figure 2A:
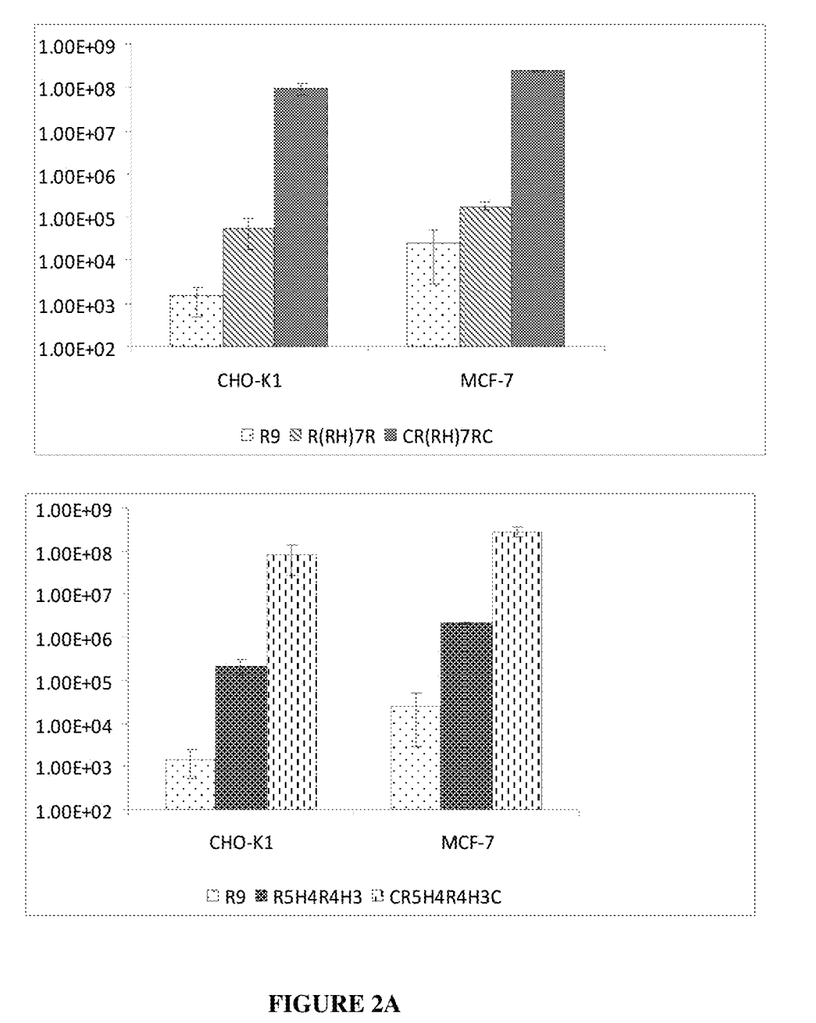
FIG. 2A: Comparison of transfection efficiency of arginines-histidine-cysteine based peptides comprising nanocomplexes with their native counterparts. The nanocomplexes were prepared using 2 µg of plasmid DNA at charge ratio 10.0 and added to cells. After 24 hrs of transfection, luciferase activity was measured and expressed as RLU/mg total protein.
Figure 2B:
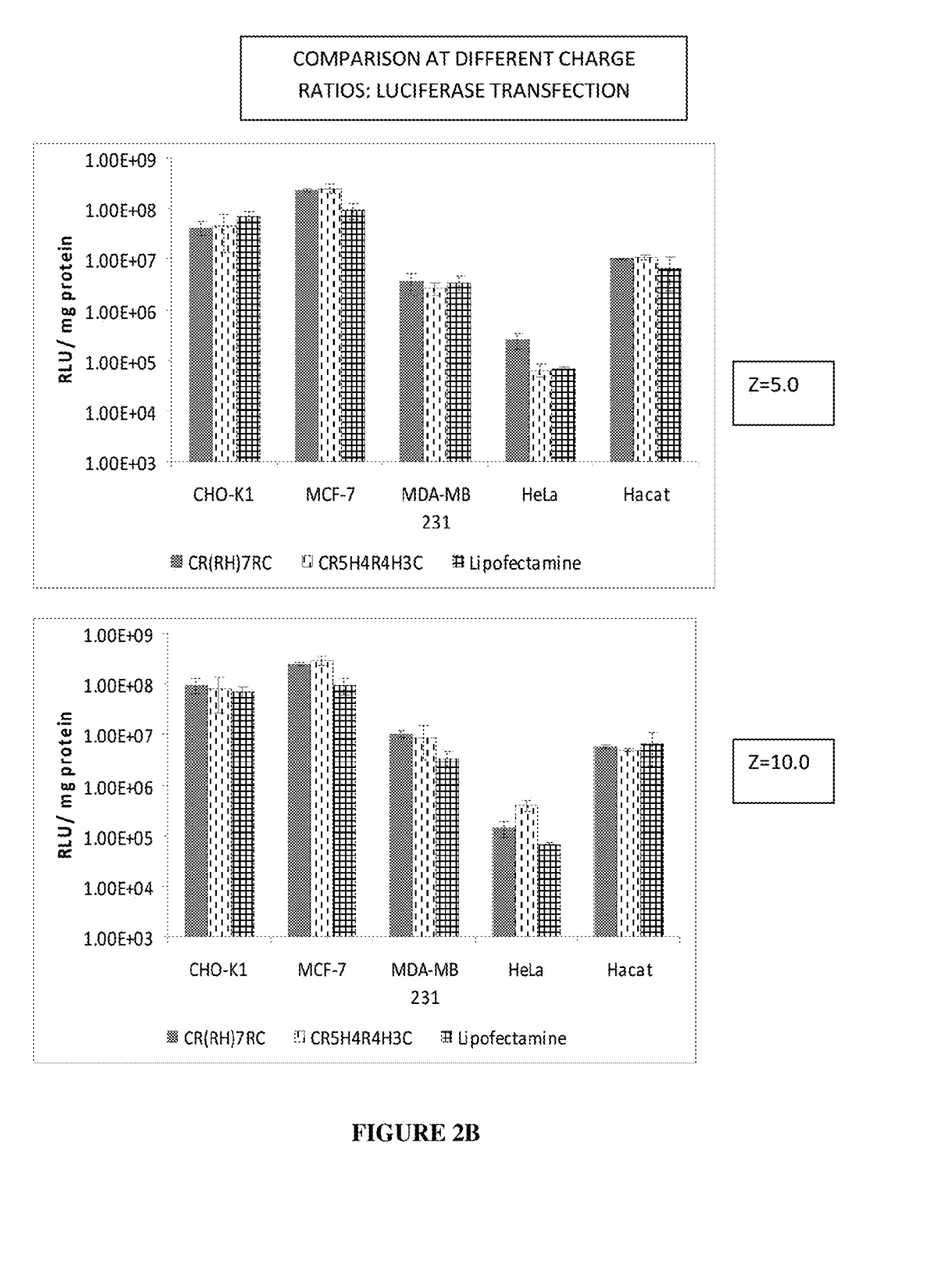
FIG. 2B: Transfection efficiency of arginines-histidine-cysteine based peptides comprising nanocomplexes in multiple cell lines at different charge ratios. The nanocomplexes were prepared using 2 µg of plasmid DNA at charge ratio 5.0 and 10.0 and added to cells. After 24 hrs of transfection, luciferase activity was measured and expressed as RLU/mg total protein.
Figure 2C:
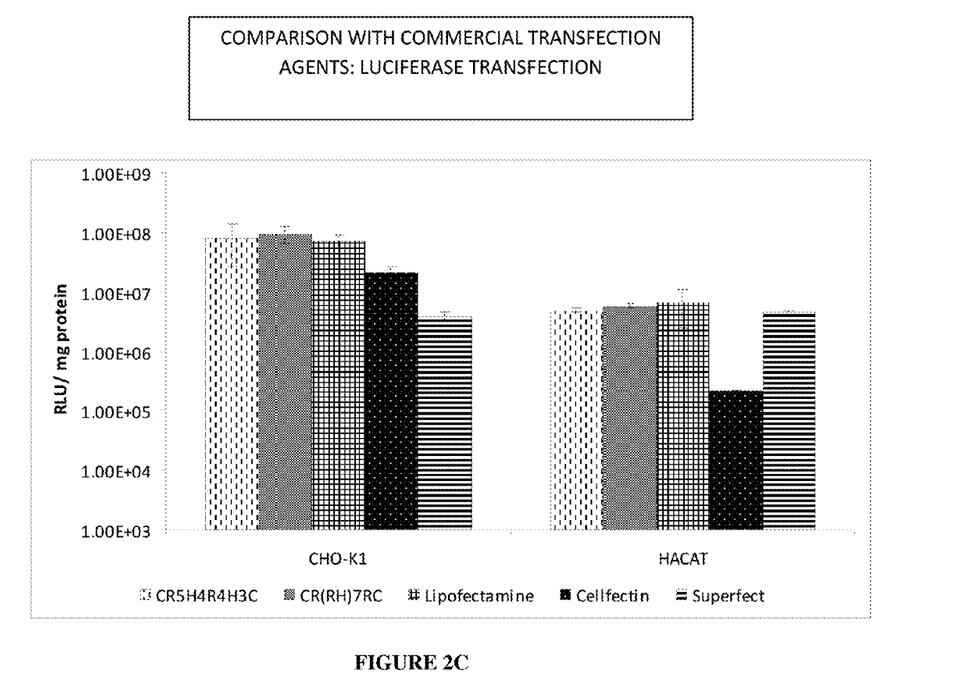
FIG. 2C: Transfection efficiency of arginines-histidine-cysteine based peptides comprising nanocomplexes in CHO-K1 and Hacat cells as compared to commercially available transfection agents. The nanocomplexes were prepared using 2 g of plasmid DNA at charge ratio 10.0 and added to cells. After 24 hrs of transfection, luciferase activity was measured and expressed as RLU/mg total protein.
Figure 3:
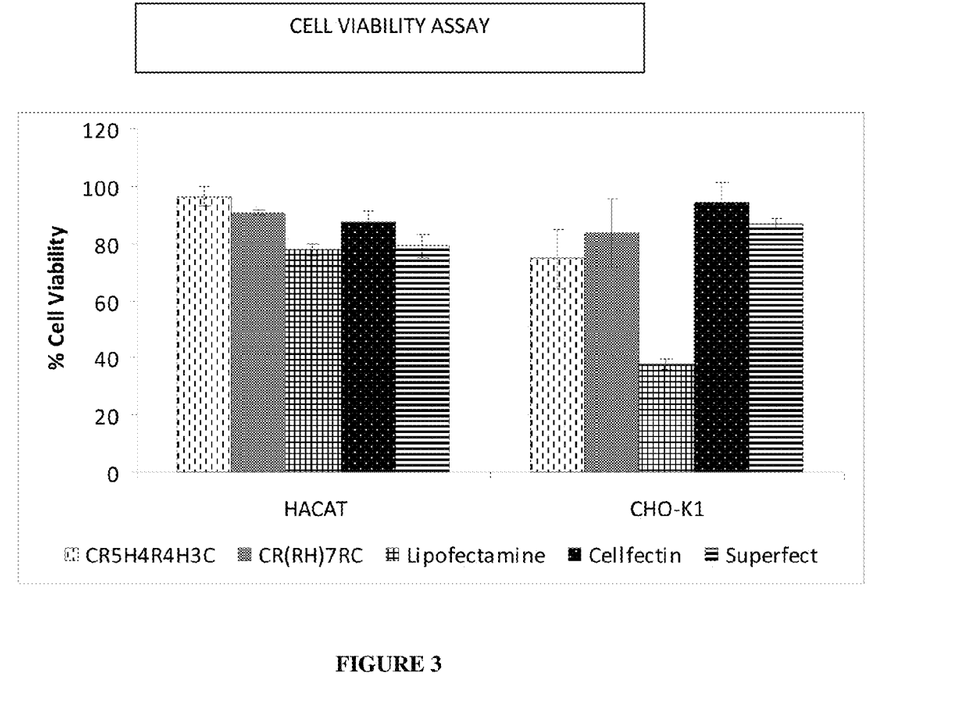
Figure 4:
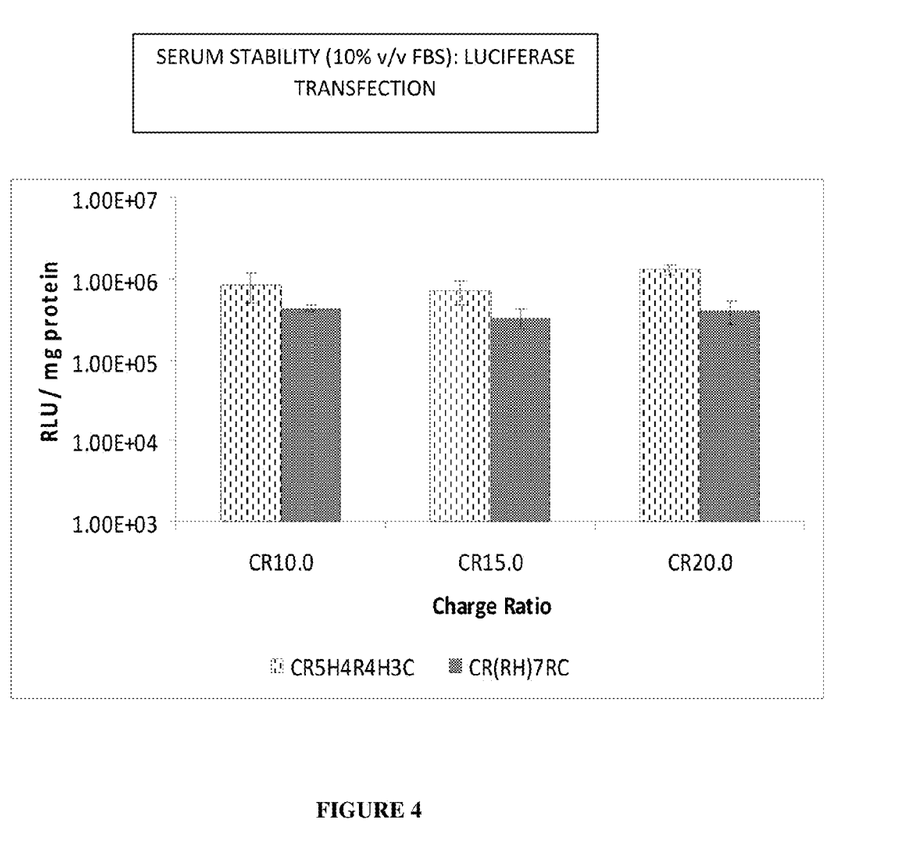
FIG. 4: Serum stability of arginines-histidine-cysteine based peptides comprising nanocomplexes in CHO-K1 cells at charge ratio 10.0; 15.0; 20.0 in presence of 10% (v/v) FBS. The nanocomplexes were prepared using 2 µg of plasmid DNA at charge ratio 10.0; 15.0; 20.0 and added to cells in presence of 10% FBS. After 24 hrs of transfection, luciferase activity was measured and expressed as RLU/mg total protein.

Present invention lies in provision of peptide based efficient nanocomplex transfection agent with optimum condensation release balance ability owing to presence of arginines, efficient endosomal escape owing to the presence of histidines and high transfection efficiency due to balanced condensation and release attributed to presence of cysteines. The most prominent and attractive features of the nanocomplex system comprise of its uniqueness in the process of synthesis whereby no prior oxidation is required and its ability to give remarkably higher transfection efficiencies without compromising cellular integrity. It not only shows equal or higher transfection ability as compared to commercially available known transfection agents but also overcomes their limitations of cumbersome synthesis procedures, cytotoxicity and increased cost.

EXAMPLES

The following examples are given by way of illustration therefore should not be construed to limit the scope of the invention.

Example 1

Peptide Design and Synthesis

The peptide sequence used to form nanocomplexes is designed using evidences from previously reported literature emphasizing the role of arginines as efficient DNA condensation moieties that can directly penetrate the cells along with incorporation of histidine residues that can overcome the endosomal barrier and cysteines for providing controlled release of cargo inside the cells. Although the residues were known for their specific roles but the optimum arrangement of the same was not known. Thus the rationale behind the order of the amino acid was based on:

1. The arrangement and number of residues forming these peptides in the nanocomplexes was deciphered from the fact that arginines ensure compact monodisperse nanocomplex formation, the histidines are involved in endosomal release and the cysteines provide further control on balanced condensation and release. This combination and number of residues has been rationally arranged to form nanocomplexes for efficient DNA delivery.
2. The ability of the peptides to form monodisperse nanocomplexes with DNA resulting in high efficiency of DNA delivery without requiring oxidative procedures. All other known cysteine based peptide constituting carrier systems require an oxidative step in order to ensure formation of pre- or post-reducible polycations for efficient gene delivery which involves cumbersome preparative procedure and problem of reproducibility.
3. The peptides forming nanocomplexes were designed to be short in length unlike the known reducible polycations of similar composition and show equivalent or better transfection efficiency and lower toxicity than the known commercial nucleic acid delivery agents (depending upon the cell line used) and also exhibit the property of serum stability.

The peptides constituting nanocomplexes were having the sequence as:

```
                            (SEQ ID NO.: 1)
CRRRRRHHHHRRRRHHHC (SEQ ID NO.: 2)
CRRHRHRHRHRHRHRHRC (SEQ ID NO.: 3)
RRRRRRRR (SEQ ID NO.: 4)
RRRRRHHHHRRRRHHH (SEQ ID NO.: 5)
RRHRHRHRHRHRHRHR
```

Peptides were synthesized by automated solid phase synthesis using Fmoc protected amino acids. The amino acid residues were activated for coupling with HBTU (O-benzotriazole-N,N,N',N',-tetramethyluroniumexafluorophosphate) and HOBt (Nhydroxybenzotriazole) in the presence of DIPEA (diisopropylethylamine). Deprotections were carried out in 2% DBU, 2% piperidine in DMF (N,Ndimethylformamide). Cleavage of the peptide from the resin was performed in Trifluoroacetic acid (TFA), Triisopropylsilane (TIPS) and water. TFA was evaporated and cleavage products were dissolved in ether. The water-soluble peptides were extracted with water and lyophilized. Peptides were purified by reversed phase HPLC, using a C-18 column. Once purified, the peptides were lyophilized to powder and peptide identity was confirmed by MALDI mass spectrometry. The yield obtained was 5-9 mg each batch and with more than 95% purity. These conditions comply with that available in the literature.

Example 2

Preparation of Nanocomplexes

Nanocomplexes were prepared at different charge ratios expressed as peptide nitrogen per nucleic acid phosphate (N/P) or as Z (+/−). The plasmid DNA stock was diluted to required working concentration range of 20-50 ng/µl and added drop-wise to an equal volume of the appropriate peptide dilutions [charge ratio (peptide conc.): 0.25 (0.43 µM); 0.5 (0.86 µM); 0.75 (1.29 µM); 1.0 (1.72 µM); 1.25 (2.15 µM); 0.5 (2.59 µM); 1.75 (3.02 µM); 2.0 (3.45µ); 3.0 (5.171 µM); 5.0 (8.62 µM); for transfection studies 5.0 (17.25 µM); 10.0 (34.7 µM); 15.0 (51.75 µM); 20 (69.4 µM)] while vortexing simultaneously. The nanocomplexes were allowed to remain undisturbed at RT for 30-60 mins to attain stability.

Example 3

Characterization of the Prepared Nanocomplexes by Assessing the Surface Morphology, Particle Size and Zeta Potential Using AFM and Zetasizer Nano-ZS Briefly nanocomplexes were prepared at charge ratios 3.0 and 5.0 respectively using 20 ng/ul plasmid DNA concentration. The surface morphology of the nanocomplexes at different charge ratios was determined by Atomic Force Microscopy using PicoSPM system operating in Acoustic mode. The nanocomplexes were imaged by simply depositing 2 ul of the nanocomplex solution on to freshly cleaved mica and drying it in air 15-20 mins at RT. Minimum image processing (first order flattening and contrast settings) was employed and image analysis was done using PicoImage software 4.1. However the nanocomplex size was measured by dynamic light scattering using Zetasizer Nano-ZS. The nanocomplex was in the size range of 50-110 nm with plasmid DNA (of sizes in the range of 3-7 kb).

Example 4

DNA Condensation Assay/Gel Retardation Assay by Varying the Amount of Peptide in Nanocomplex The electrostatic interaction between the positively charged peptide and negatively charged plasmid DNA results in neutralization of negative charges of plasmid DNA, which subsequently retards its mobility under the influence of electric field. To determine the optimal concentration of peptide required for complete retardation of DNA, the nanocomplex was prepared at different charge ratios, keeping the amount of plasmid DNA constant, and retardation was analyzed on 1% agarose gel. To prepare the plasmid DNA was mixed with peptide at following charge ratios (0.5, 0.75, 1, 1.25, 1.5, 1.75, 2.0, 3.0, 5.0) and incubated for 30 mins at RT. After incubation period was over, the nanocomplex was mixed with the loading dye (1×) and electrophoresed at 110V for 45 mins in TAE (1×) buffer. The gels were stained by EtBr (0.2 mg/ml) and the bands corresponding to plasmid DNA were visualized using Syngene Gel Doc system while images were recorded using Gene Snap software. The nanocomplex system maintains condensation at charge ratio=1.5-2.0 to protect the nucleic acid.

Example 5

DNA Release Assay/Gel Release Assay by Varying the Amount of Anionic Agent with Respect to Peptide in the Nanocomplex and Comparing the Amount of Plasmid DNA Released with Respect to Native Uncomplexed Plasmid DNA Nanocomplex was prepared at charge ratio Z (+/−) 10.0 and kept for 30 mins at RT to attain stability. Heparin was then added in increasing amounts ranging from wt/wt ratios (anionic agent/peptide) of 0.25:1 to 2:1 and complexes were further incubated at RT for 30 mins. After incubation period was over, the nanocomplex was mixed with the loading dye (1×) and electrophoresed at 110V for 45 mins in TAE (1×) buffer. The gels were stained by EtBr (0.2 mg/ml) and the bands corresponding to plasmid DNA were visualized using Syngene Gel Doc system while images were recorded using Gene Snap software. The nanocomplex system maintains release at wt. of anionic agent/wt. of peptide ratio=0.5-1.0 to relieve cargo appropriately inside the cell.

Example 6

Fluorimetric Measurement of DNA Condensation

The experiment was performed in 96 well plate format where 10 ul ethidium bromide (4.22 ng/ul) and 20 ul plasmid DNA was dispensed in each well and incubated in dark for 5 mins at RT. This was followed by addition of 20 ul peptide solution corresponding to different charge ratios and plate was incubated for further 15 mins in dark. Fluorescence was recorded using 535 SL EXP 1 excitation and 595 SL EMP 1 emission filters (Beckman Coulter plate reader, DTX 880, USA). The fluorescence values of plasmid DNA with EtBr were taken as maximum i.e. 100% and the relative percentage decrease in fluorescence signal was calculated at increasing charge ratios and plotted as percentage of maximum (% of Max.). The nanocomplex system maintains condensation at charge ratio=1.5-2.0 to protect the nucleic acid.

Example 7

Fluorimetric Estimation of DNA Release Ability of the Nanocomplex

The experiment was performed in 96 well plate format where heparin was added at increasing amount to different wells followed by addition of 20 ul of nanocomplexes (Z=10). EtBr was added to each of the wells at concentration of 4.22 ng/ul. The plate was incubated in dark for 15 mins. The fluorescence was recorded using 535SL EXP1 excitation and 595 SL EMP1 emission filters (Beckman Coulter plate reader, DTX 880, USA). The fluorescence values of plasmid DNA with EtBr were taken as maximum i.e. 100% and the relative percentage increase in fluorescence signal was calculated at increasing concentration of heparin and was plotted as percentage of maximum (% of Max.). The nanocomplex system maintains release at wt. of anionic agent/wt. of peptide ratio=0.5-1.0 to relieve cargo appropriately inside the cell.

Example 8

Assessment of the Transfection Efficiency of the Nanocomplex in Various Cell Lines CHO-K1 cells were maintained in HamsF12K media, HeLa in MEM, breast cancer cells MCF-7 and MDA-MB231 were cultured in DMEM and Hacat cells were maintained in DMEM-F12 media respectively, all supplemented with 10% (v/v) FBS at 37° C. and 5% $CO_2$ in humidified incubator. Cells were seeded in 24 well plate format and the experiment was conducted after 24 hours when a confluency of 70% was reached. Nanocomplexes were prepared at charge ratio 5.0 and 10.0 respectively with final plasmid DNA concentration of 40 ng/ul (pMIR-Report™ Luciferase) and incubated for one hour. 100 ul of nanocomplex (2 ug plasmid/well) was added to the cells in serum free media (Opti MEM). After 5 hours of incubation the media containing nanocomplex was aspirated and cells were rinsed with 1×PBS (pH=7.4) and finally supplemented with complete growth medium. After 24 hrs of transfection, cells were lysed with 100 ul of cell culture lysis buffer (1×CCLR) and luciferase activity was measured by mixing luciferase assay substrate and cell lysate in 1:1 ratio using a luminometer (Berthold detection system, Germany). Transfection efficiency was normalized with total protein content of the cells, estimated using bicinchoninic acid assay (BCA). Transfection efficiency is presented as mean value±standard deviation of three independent experiments each performed in duplicates. The nanocomplexes give maximal transfection efficiency of 7-9 orders in RLU/mg protein in multiple cell lines.

| Cell lines | Cell line repository | Catalogue number |
|---|---|---|
| CHO-K1 | ATCC | CCL-61 |
| MCF-7 | ATCC | HTB-22 |
| MD-MB231 | ATCC | HTB-26 |
| HeLa | ATCC | CCL-2 |
| HACAT | CLS Cell line services, Germany | CLS order number 300493 |

Example 9

Assessment of the Transfection Efficiency of the Nanocomplex in Hacat Cells as Compared to Commercial Agents Hacat cells were maintained in DMEM-F12 media supplemented with 10% (v/v) FBS at 37° C. and 5% $CO_2$ in humidified incubator. Cells were seeded in 24 well plate format and the experiment was conducted after 24 hours when a confluency of 70% was reached. Nanocomplexes were prepared at charge ratio 10.0 with final plasmid DNA concentration of 40 ng/ul (pMIR-Report™ Luciferase) and incubated for one hour. Complexes with Lipofectamine 2000™, Cellfectin™ and Superfect™ were prepared in 2:1 ratio (commercial agent:plasmid DNA) and incubated at RT for 30 mins. 100 ul of nanocomplex (2 ug plasmid/well) was added to the cells in serum free media (Opti MEM). After 5 hours of incubation the media containing nanocomplex was aspirated and cells were rinsed with 1×PBS (pH=7.4) and finally supplemented with complete growth medium. After 24 hrs of transfection, cells were lysed with 100 ul of cell culture lysis buffer (1×CCLR) and luciferase activity was measured by mixing luciferase assay substrate and cell lysate in 1:1 ratio using a luminometer (Berthold detection system, Germany). Transfection efficiency was normalized with total protein content of the cells, estimated using bicinchoninic acid assay (BCA). Transfection efficiency is presented as mean value±standard deviation of three independent experiments each performed in duplicates. The nanocomplexes give maximal transfection efficiency similar to Lipofectamine and 1.5-2 folds higher than cellfectin and superfect.

Example 10

The Cytotoxicity of Nanocomplex Using MTT Assay

CHO-K1 cells were seeded at density of 7000 cells per well in 96 well plate format in Hams F12K media containing 10% FBS at 37° C. and 5% $CO_2$ in humidified incubator. After 24 hours cells were washed with serum free media and treated with different nanocomplex at Z=10.0 (in quadruplets) for 4 hours, keeping DNA concentration 200 ng/well. The viability was assayed after 4 hrs and 24 hrs (in the latter case nanocomplex containing media was replaced with complete media after 4 hrs) of transfection. Briefly 100 ul of MTT reagent (0.5 mg/ml) was added to each well and incubated at 37° C. for 2 hrs to allow formation of formazan crystals. The media containing the MTT reagent was decanted carefully from the wells such that the crystals do not get detached. Following incubation 100 ul MTT detergent buffer (0.5 ml 10% SDS and 0.06 ml 12N HCl in 10 ml isopropanol) was added to each well and crystals were dissolved by gentle shaking for 30 mins. Finally the absorbance was recorded at 550 nm and 670 nm (to negate debris) along with the blank using ELISA plate reader. The percentage viability was calculated by Treated wells (OD550–OD670)/Untreated well (OD550–OD670)*100. The average of two independent experiments is plotted where each treatment is performed in quadruplets. Nanocomplexes exhibit cell viability of 80-100%.

Example 11

Cytotoxicity Estimation Using Celltitre GLO Method Based on the Estimation of ATP Activity of Viable Cells The experiment was performed in 96 well plate format wherein the Hacat cells were seeded at 50000 cells per well in DMEM-F12 media containing 10% FBS at 37° C. and 5% $CO_2$ in humidified incubator. After 24 hours cells were washed with serum free media and treated with nanocomplex at Z=10.0 (in quadruplets) for 4 hours, keeping DNA concentration 200 ng/well. The viability was assayed after 4 hrs and 24 hrs (in the latter case nanocomplex containing media was replaced with complete media after 4 hrs) of transfection. Initially the plate was equilibrated for 30 mins at RT followed by addition of 100 ul of cell titre GLO reagent with continuous shaking on rotor for 2 mins to allow cell lysis. The plate was then kept in dark for 10 mins at RT for stabilization of the luminescence signal. The reading was recorded on Tecan system and plotted as % cell viability. Nanocomplex exhibit cell viability of 80-100%.

Example 12

Assessment of the Serum Stability of the Nanocomplex in CHO-K1 Cells as Compared to Commercial Agents CHO-K1 cells were maintained in Hams-F12k media supplemented with 10% (v/v) FBS at 37° C. and 5% $CO_2$ in humidified incubator. Cells were seeded in 24 well plate formats and the experiment was conducted after 24 hours when a confluency of 70% was reached. Nanocomplex was prepared at charge ratio 10.0; 15.0 and 20.0 with final plasmid DNA concentration of 40 ng/ul (pMIR-Report™ Luciferase) and incubated for one hour. 100 ul of nanocomplex (2 ug plasmid/well) was added to the cells in complete media (Hams-F12k) with 10% FBS. After 5 hours of incubation the media containing nanocomplex was aspirated and cells were rinsed with 1×PBS (pH=7.4) and finally again supplemented with complete growth medium. After 24 hrs of transfection, cells were lysed with 100 ul of cell culture lysis buffer (1×CCLR) and luciferase activity was measured by mixing luciferase assay substrate and cell lysate in 1:1 ratio using a luminometer (Berthold detection system, Germany). Transfection efficiency was normalized with total protein content of the cells, estimated using bicinchoninic acid assay (BCA). Transfection efficiency is presented as mean value±standard deviation of three independent experiments each performed in duplicates. Nanocomplexes exhibit serum stability and give consistently high transfection efficiency [5-7 orders in RLU/mg protein] in the presence of 10% serum concentration.

Advantages of Invention

- The nanocomplex comprising arginine, histidine and cysteine based peptide is an efficient nucleic acid delivery vector.
- It is easy to synthesize and economical to use.
- It has the ability to transfect a variety of cell line systems such as CHO-K1, MCF-7, MDA-MB231, HeLa, Hacat.
- Transfection efficiency of nanocomplex containing arginine, histidine and cysteine based peptide system is higher [transfection efficiency 6-8 orders in RLU/mg protein] with respect to commercially available known transfection agents in most cell lines and comparable in few more [transfection efficiency 5-8 orders in RLU/mg protein].
- The nanocomplex system carries no or less observed cytotoxicity [80-100% cell viability] compared to some other known transfection agents [50-70% cell viability] hence it has the potential to be used for in vivo studies.
- The peptide nanocomplex transfection system exhibits serum stability (10% serum concentration) and hence can be used for systemic delivery based therapeutic applications.

REFERENCES

El-Sayed A, Futaki S, Harashima H. Delivery of macromolecules usinf arginine-rich cell-penetrating peptides: ways to overcome endosomal entrapment. AAPS J. 2009; 11: 1322.

Hart S L. Multifunctional nanocomplexes for gene transfer and gene therapy. Cell Biol. Toxicol. 2010; 26: 69-81.

Howard K A. Delivery of RNA interference therapeutics using polycation-based nanoparticles. Adv. Drug Delivery Rev. 2009; 61: 710-720.

Lo S L, Wang S. An endosomolytic Tat peptide produced by incorporation of histidine and cysteine residues as a nonviral vector for DNA transfection. Biomaterials 2008; 29: 2408-2414.

Mann A, Thakur G, Shukla V, Ganguli M. Peptide in DNA delivery: current insights and future directions. Drug Discovery Today 2007; 13: 152-160.

Mann A, Thakur G, Shukla V, Singh A K, Khanduri R, Naik R, Jiand Y, Kalara N, Dwarakanath B S, Langel U, Ganguli M. Differences in DNA condensation and release by lysine and arginine homopeptides govern their DNA delivery efficiencies. Mol. Pharmaceutics. 2011; 10.1021/mp2000814

Martin M E, Rice K G. Peptide-guided gene delivery. AAPS J. 2007; 9: E18-29.

Midoux P, Pichon C, Yaouanc J J, Jaffrs P A. Chemical vectors for gene delivery: a current review on polymers, peptides and lipids containing histidine or imidazole as nucleic acids carriers. Br. J. Pharmacol. 2009; 157: 166-178.

Mintzer M A, Simanek E E. Nonviral vectors for gene delivery. Chem Rev. 2009; 109: 259-302.

Morris M C, Chaloin L, Heitz F, Divita G. Translocating peptides and proteins and their use for gene delivery. Curr. Opin. Biotehnol. 2000; 11: 461-466.

Petros R A, DeSimone J M. Strategies in the design of nanoparticles for therapeutic applications. Nat. Rev. Drug Discovery 2010; 9: 615-627.

Remaut K, Sanders N N, De Geest B G, Braeckmans K, Demeester J, De Smedt S C. Nucleic acid delivery: Where material sciences and bio-sciences meet. Mater. Sci. Eng., R. 2007; 58: 117-161.

Rubanyi G M. The future of human gene therapy. Mol Aspects Med. 2001; 22: 113-142.

Saccardo P, Villaverde A, González-Montalbán N. Peptide-mediated DNA condensation for non-viral gene therapy. Biotechnol. Adv. 2009; 27: 432-438.

Vázquez E, Ferrer-Miralles N, Vimmaverde A. Peptide-assisted traffic engineering for nonviral gene therapy. Drug Discovery Today 2008; 13: 1067-1074.

Won Y W, Kim H A, Lee M, Kim Y H. Reducible Poly (oligo-D-arginine) for enhanced gene expression in mouse lung by intratracheal injection. Mol. Ther. 2010; 18: 734-742.

Won Y W, Yoon S M, Lee K M, Kim Y H. Poly(oligo-D-arginine) with internal disulfide linkages as a cytoplasm sensitive carrier for siRNA delivery. Mol. Ther. 2011; 19: 372-380.

We claim:

1. A nanocomplex containing cationic peptide CR$_5$H$_4$R$_4$H$_3$C (SEQ ID NO.: 1) and CR(RH)$_7$RC (SEQ ID NO.: 2).

2. The nanocomplex as claimed in claim 1 further comprising a biomolecule is selected from the group comprising of a DNA, RNA, an antisense nucleotide, an aptamer, a protein, a glycoprotein, a polypeptide, a carbohydrate or a mixture or adduct of any two or more of these.

3. The biomolecule as claimed in claim 2, wherein the size of the biomolecule is in the range of 3 kbp to 7 kbp for nucleic acids.

4. The nanocomplex as claimed in claim 1 having a maximal transfection efficiency of 7-9 orders in RLU/mg protein with minimal cytotoxicity.

5. The nanocomplex as claimed in claim 1 having a size in the range of 50-110 nm.

6. A method for transfection of a cell using the nanocomplex as claimed in claim 1 characterized in having no prior oxidation step on either the peptide or the nanocomplex at any preparative step involved.

7. A method of preparing the nanocomplex as claimed in claim 1, comprising:
   (a) providing SEQ ID NO.:1 and SEQ ID NO.: 2;
   (b) providing a biomolecule selected from the group comprising of a DNA, RNA, an antisense nucleotide, an aptamer, a protein, a glycoprotein, a polypeptide, a carbohydrate or a mixture or adduct of any two or more of these;
   (c) diluting the peptide 10-100 µl obtained in step (a) and DNA 20-50 ng/µl obtained in step (b) in water such that peptide-DNA charge ratio is 0.25-20;
   (d) adding DNA solution obtained in step (b) drop-wise to an equal volume of the peptide dilution while vortexing; and
   (e) incubating solution obtained in step (d) for 30 min to 1 h at room temperature.

8. A kit useful for delivering biomolecules into a cell, said kit comprising peptides as claimed in claim 1 and an instruction manual.

9. A method for delivery of nucleic acids into cells, comprising:
   providing a composition comprising the nanocomplex as claimed in claim 1, wherein the nanocomplex comprises isolated nucleic acid selected for delivery to cells; and
   contacting cells with an amount of the composition effective to deliver the isolated nucleic acids into the cells.

10. A method for delivery of proteins to cells, comprising:
    providing a composition comprising the nanocomplex as claimed in claim 1 wherein the nanocomplex comprises isolated protein selected for delivery to cells; and
    contacting cells with an amount of the composition effective to deliver the isolated protein into the cells.

11. A method for delivery of biomolecules to cells, comprising:
    providing a composition comprising the nanocomplex as claimed in claim 1, wherein the nanocomplex comprises isolated biomolecules selected for delivery to cells; and
    contacting cells with an amount of the composition effective to deliver the isolated biomolecules to the cells.

12. The method of claim 11 wherein the cells are eukaryotic cells.

13. The method of claim 11 wherein the eukaryotic cells are cultured in a serum containing medium.

* * * * *

SEQUENCE LISTING

```
<160> NUMBER OF SEQ ID NOS: 5

<210> SEQ ID NO 1
<211> LENGTH: 18
<212> TYPE: PRT
<213> ORGANISM: Artificial Sequence
<220> FEATURE:
<223> OTHER INFORMATION: A synthetic polypeptide

<400> SEQUENCE: 1

Cys Arg Arg Arg Arg Arg His His His His Arg Arg Arg Arg His His
1               5                   10                  15

His Cys

<210> SEQ ID NO 2
<211> LENGTH: 18
<212> TYPE: PRT
<213> ORGANISM: Artificial Sequence
<220> FEATURE:
<223> OTHER INFORMATION: A synthetic polypeptide

<400> SEQUENCE: 2

Cys Arg Arg His Arg His Arg His Arg His Arg His Arg His Arg His
1               5                   10                  15

Arg Cys

<210> SEQ ID NO 3
<211> LENGTH: 9
<212> TYPE: PRT
<213> ORGANISM: Artificial Sequence
<220> FEATURE:
<223> OTHER INFORMATION: A synthetic polypeptide

<400> SEQUENCE: 3

Arg Arg Arg Arg Arg Arg Arg Arg Arg
1               5

<210> SEQ ID NO 4
<211> LENGTH: 16
<212> TYPE: PRT
<213> ORGANISM: Artificial Sequence
<220> FEATURE:
<223> OTHER INFORMATION: A synthetic polypeptide

<400> SEQUENCE: 4
```

```
Arg Arg Arg Arg Arg His His His Arg Arg Arg Arg His His His
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: A synthetic polypeptide

<400> SEQUENCE: 5

Arg Arg His Arg His Arg His Arg His Arg His Arg His Arg His Arg
1               5                   10                  15
```